United States Patent [19]

Palti

[11] Patent Number: 5,529,066
[45] Date of Patent: Jun. 25, 1996

[54] IMPLANTABLE CAPSULE FOR ENHANCING CELL ELECTRIC SIGNALS

[75] Inventor: Yoram Palti, Haifa, Israel

[73] Assignee: CB-Carmel Biotechnology Ltd., Israel

[21] Appl. No.: 266,204

[22] Filed: Jun. 27, 1994

[51] Int. Cl.⁶ ............................................. A61B 5/05
[52] U.S. Cl. .................. 128/635; 204/403; 204/415; 264/4; 424/424; 604/50
[58] Field of Search ............................ 424/424; 128/630, 128/632, 635, 899; 204/403, 415; 604/50; 264/4

[56] References Cited

U.S. PATENT DOCUMENTS

| | | | |
|---|---|---|---|
| 4,251,387 | 2/1981 | Lim et al. | 264/4 |
| 4,391,909 | 7/1983 | Lim | 264/4 |
| 4,436,094 | 3/1984 | Cerami | 128/635 |
| 4,479,796 | 10/1984 | Kallok | 424/424 |
| 4,650,547 | 3/1987 | Gough | 128/635 |
| 4,662,996 | 5/1987 | Venkatasetty | 204/415 |
| 4,689,293 | 8/1987 | Goosen et al. | 424/424 |
| 4,803,168 | 2/1989 | Jarvis, Jr. | 264/4 |
| 5,101,814 | 4/1992 | Palti . | |
| 5,190,041 | 3/1993 | Palti . | |
| 5,344,454 | 9/1994 | Clarke et al. | 424/424 |
| 5,368,028 | 11/1994 | Palti | 128/635 |

FOREIGN PATENT DOCUMENTS

| | | | |
|---|---|---|---|
| 9213271 | 8/1992 | WIPO | 204/403 |

*Primary Examiner*—Angela D. Sykes
*Assistant Examiner*—Eric F. Winakur
*Attorney, Agent, or Firm*—Bryan Cave; David M. Klein

[57] ABSTRACT

A capsule for encapsulating implantable cells for improving the detectability of electrical signals generated by the cells is provided. The capsule includes a low-conductivity (high electrical resistance) membrane and a semi-permeable (low electrical resistance) membrane. The low-conductivity membrane seals around the circumference of the cell mass between the electrical poles of the capsule, and further extends for increasing the electrical resistance between the poles. The semi-permeable membrane enables nutrients and waste materials to flow to and from the cell mass. The semi-permeable membrane encloses at least one of the poles of the cell mass, and cooperates with the low-conductivity membrane to completely enclose the cell mass. The low-conductivity membrane may enclose one of the poles, if desired. Electrodes are used to detect the electrical signals from the cell mass. Various methods of making the capsule are disclosed.

13 Claims, 7 Drawing Sheets

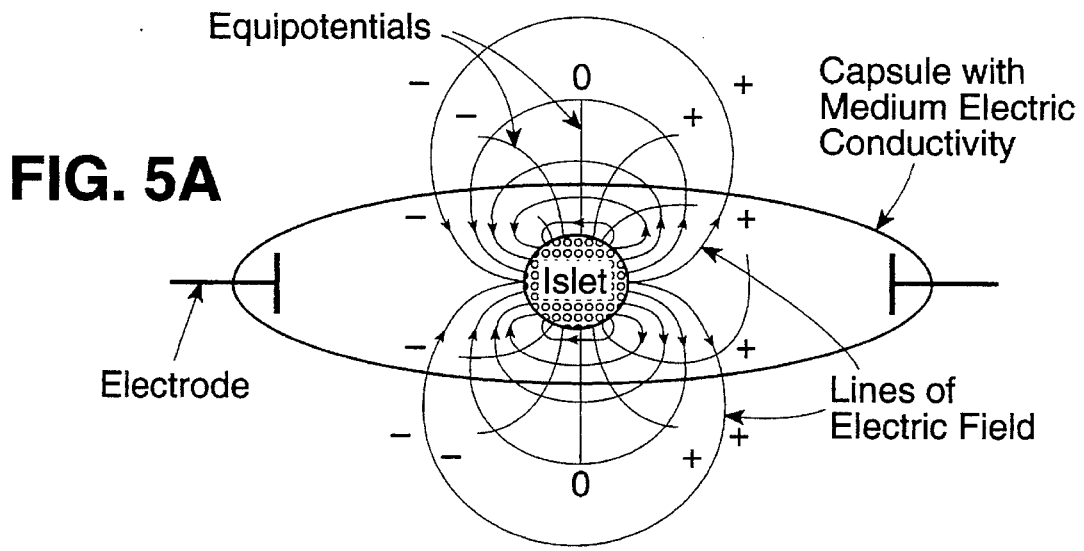
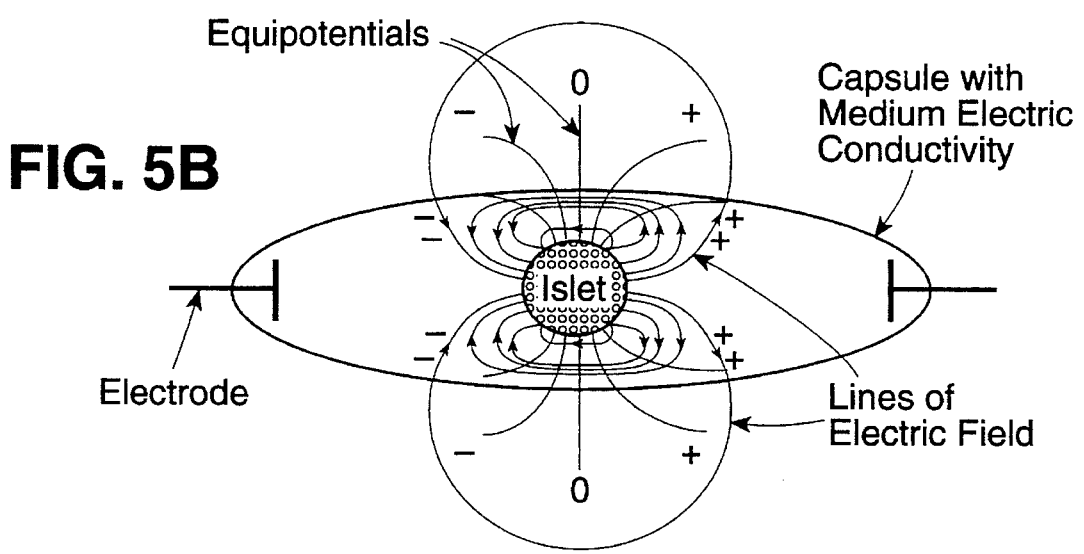
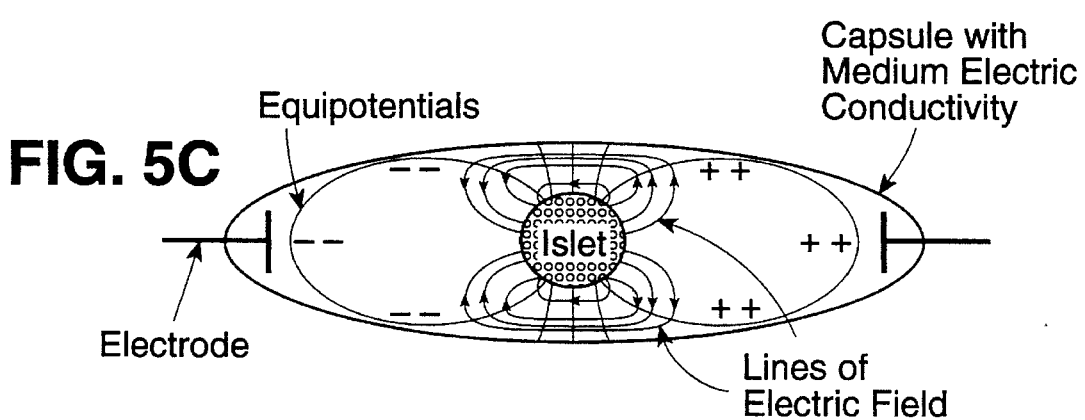

IMPLANTABLE CAPSULE FOR ENHANCING CELL ELECTRIC SIGNALS

BACKGROUND OF THE INVENTION

1. Field of the Invention

The present invention relates to a capsule for encapsulating implantable cells for improving the detectability of electrical signals generated by the cells. The invention also relates to a method of making the capsule, and a constituent detection system in which the capsule is used.

2. Description of the Related Art

The immune system is responsible for the phenomenon of rejection, i.e. destruction of cells or tissues taken from one person or species and implanted in another. The rejection is stronger when the implant's origin is from another species. To reduce this problem in human-to-human or animal-to-animal implants, tissue type matching procedures are employed and intensive immuno-suppressive drug treatment is given to the recipient, usually for life.

An alternative technique that enables autografting (in the same species), as well as xenografting (between different species) is to enclose the implant in a sealed capsule made out of semi-permeable membrane. The membrane is permeable to small molecules and impermeable to large molecules. The cut-off permeability level is usually at molecular weights of about 30,000–50,000. This cut-off level allows nutrients, gases, excretions etc. to pass through the membrane into and out of the implanted cells, and at the same time prevents cells and large molecules, such as proteins and antibodies, from passing through the membrane. This method effectively neutralizes the damaging effects of the immune system. The semi-permeable membranes discriminate between substances by means of sub-microscopic pores, usually 5–50A° in diameter. Examples of such bio-compatible membrane materials include PSF (polysulfone) and PVC/PAN (polyvinylchloride/polyacrylonitrile) polymers. Such membranes are available commercially, for example, in the shape of hollow fibers of various diameters.

Commonly owned U.S. Pat. No. 5,101,814 and 5,190,041, and U.S. patent application Ser. No. 08/077,893, the contents of which are incorporated herein by reference, disclose methods by which the electrical activity of living cells encapsulated in a biocompatible semi-permeable membrane of the type discussed above may be measured. This electrical activity may be used to determine the concentration of various constituents in the medium that surrounds the cells or capsule. FIG. 1 shows an example of a recording of the electric potential changes generated by an encapsulated islet of pancreatic beta cells (some alpha and gamma cells may also be incorporated in the islet) responding to a high concentration of glucose in the medium. These electric signals can be measured by electrodes within the membrane capsule, or in its vicinity outside the capsule.

The electric signals generated by the cells are attenuated by the relatively low resistance of the medium as well as the low but significant conductivity of the membrane. The membrane is designed to allow the essential nutrients, gases, excretions etc. to enter or exit the membrane enclosure. Therefore, it is also highly permeable to the ions that make up the electrolytic physiological solution mainly: Na+, K+, Ca++, H+, Mg++, Cl–, OH–, HCOO⁻ etc. As these ions carry electric current, the electric resistance of the membrane, which separates the active living cells from the surrounding electrolyte medium, is not high enough to prevent the short-circuiting effect of the medium. For example, a typical hollow fiber membrane made of PVC, 200μ in diameter, 50μ thick and 1 cm long has an electric resistance (measured from the inside to the outside) of only 2000–5000Ω. This resistance partially short circuits the electrical signal from the cell mass and makes it difficult to detect the electric signal in the vicinity of the cell mass. Accordingly, a need exists for increasing the electrical resistance of the membrane enclosure to improve the detectability of the signals generated by the cells.

It is an object of the present invention to reduce this short circuiting effect and to thereby increase the measurability of the electrical signals generated by the cell mass.

SUMMARY OF THE INVENTION

The present invention is a capsule for surrounding an implantable cell mass. The capsule increases the electrical resistance between electrical poles on the cell mass, and thereby improves the ability to detect an electrical signal generated by the cells. The living cells may be any types of cells which produce an electrical signal, such as a potential difference, between at least a first pole on the cell mass and at least a second pole on the cell mass. The signal may be in response to the presence of a constituent in a medium surrounding the cells or a condition, i.e. pressure or temperature.

The capsule includes a membrane having a low electrical conductivity having an inner surface in sealing contact with the outer surface of the cell mass along a circumference of the cell mass between the poles. The seal reduces or prevents short circuiting between the poles by preventing the conductive medium surrounding the cell mass from providing a short circuit path between the poles adjacent to the outer surface of the cell mass. The low-conductivity membrane also co-extends with one or more of the poles for further increasing the electrical resistance between the poles.

The capsule includes a semi-permeable membrane having submicroscopic pores for enabling nutrients and cellular excretions to flow to and from the cell mass. The semi-permeable membrane encloses at least one of the poles of the cell mass, and cooperates with the low-conductivity membrane to completely enclose the cell mass. Electrodes are provided for detecting the electrical signal generated by the cell mass.

In a preferred embodiment, the low-conductivity membrane is a cylindrical ring made of a nonconductive or a low-conductive material which is bio-compatible.

Several different methods may be used to make the capsule. In one method, the capsule is formed of a non-permeable low-conductive material, and pores are formed in the portions of the capsule which are to constitute the semi-permeable membrane. In the alternative, the low-conductivity membrane may be a thick layer of the semi-permeable material, which has a lower conductivity. In another alternative, the initial membrane is semi-permeable, and the portion of the capsule which is to constitute the low-conductivity membrane is coated or plated with a material having a low-conductivity. The low-conductivity membrane and the semi-permeable membrane may be separate components, which are joined by adhesive or laminated to one another to form the capsule.

BRIEF DESCRIPTION OF THE DRAWINGS

FIGS. 5A–5C show schematic views of the electrical fields generated by islets when detecting constituent levels, while the islets are encapsulated in various types of capsules.

DESCRIPTION OF THE PREFERRED EMBODIMENT

The present invention is a membrane capsule structure that encapsulates a living cell mass, e.g., islets of Langerhans. Cells of this type are sensitive to the presence of particular constituents or conditions, and generate an electrical signal in the presence of the constituent or condition to which the cells are sensitive. The constituent may be, for example, be glucose in the blood stream of a patient. The condition may, for example, be blood pressure or bodily temperature. The electrical signal is generally a voltage or potential difference, but may be any other type of electrical signal, such as a current or a signal characterized by a particular frequency. The electrical signal is generated between electrical poles on the cell mass, such as the + and − poles shown in FIGS. 2–6. While each cell mass is shown having two poles, a cell mass may have more than two poles, i.e., the cell mass may generate multiple voltages, currents, or other electrical signals between multiple poles on the surface of the cell mass.

FIG. 5A depicts the electric field between the poles of the cell mass inside and in the vicinity of a capsule with a membrane of a relatively high electric conductivity, i.e., low resistance. The electric field spreads to the volume conductor which partially short circuits the field. As shown in FIG. 5B, this short circuiting effect is smaller when the membrane conductivity is lower. When the capsule is electrically insulated there is no external short circuiting, as shown in FIG. 5C. Under these conditions the potential difference that the two internal electrodes see is maximized and a smaller mass of cells is necessary to generate a detectable electrical signal.

Figure 1:
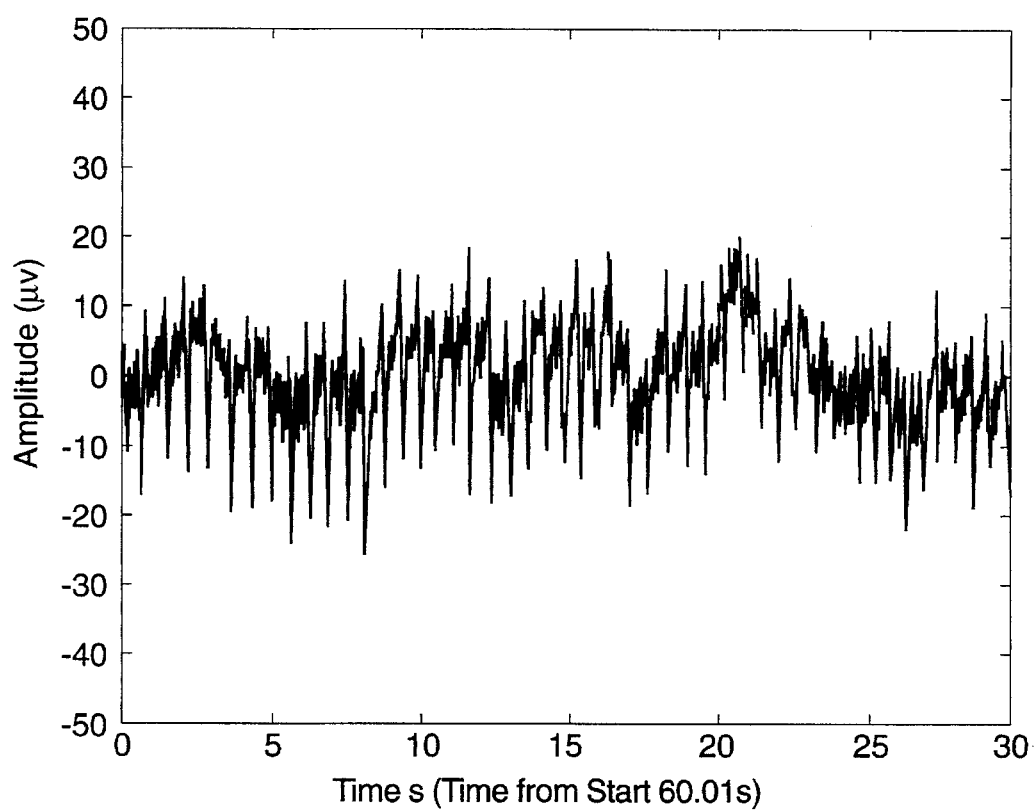
FIG. 1 shows a graph of a sample electrical signal detected from a mass of encapsulated pancreatic beta cells.
Figure 2:
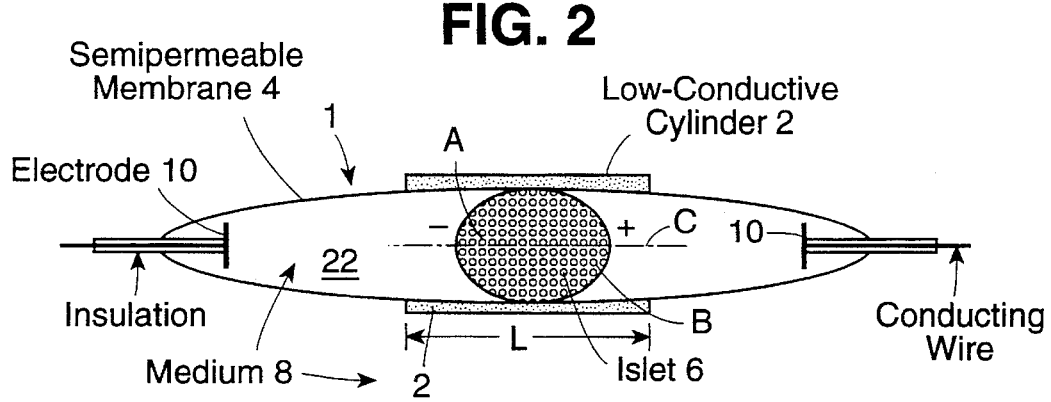
FIG. 2 shows a schematic view of a cell mass encapsulated in the capsule of the present invention.
Figure 3:
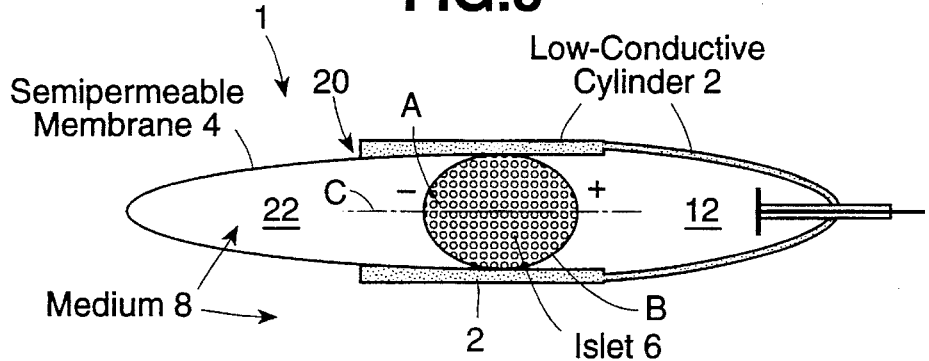
FIG. 3 shows a schematic view of a cell mass encapsulated in an alternative embodiment of the capsule of the present invention.
Figure 4:
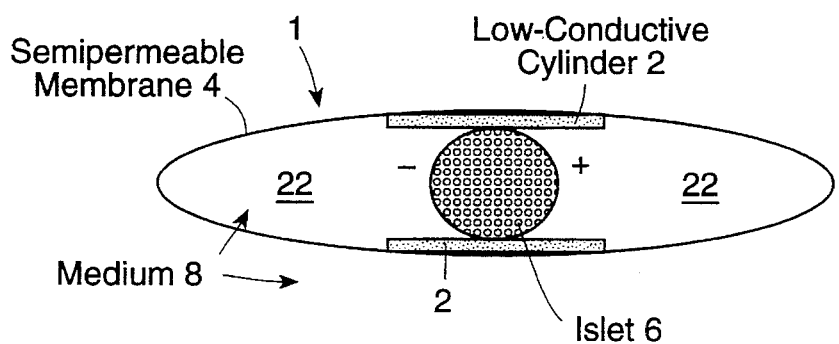
FIG. 4 shows a schematic view of a cell mass encapsulated in another alternative embodiment of the capsule of the present invention.

As shown in FIGS. 2–4, a capsule 1 encapsulates a mass of cells 6 in a manner which enables the cell mass 6 to receive adequate nutrients for survival, but which minimizes or eliminates short circuiting between at least one pair of the + and − poles of the cell mass 6. The cell mass 6 is immersed in an electrolytic medium 8, other physiological media or in a tissue. Membrane capsule 1 includes a low-conductivity membrane 2 and a semi-permeable membrane 4.

The low-conductivity membrane 2 has an inner diameter closely sized to the diameter of the cell mass 6 for sealingly engaging the cell mass 6 along a circumference of the cell mass between the + and − poles for increasing the electric resistance between the + and − poles. The low-conductivity membrane has a length L substantially co-extending with a polar axis C between the + and − poles of the cell mass for increasing the electrical resistance therebetween. The longer the length L, the higher the electrical resistance between the poles. The cell mass 6 may have non-uniform shapes, and the poles may be positioned on different positions on the cell mass. Accordingly, the polar axis C may be any axis which runs between the poles such that a low-conductivity membrane 2 may be positioned on the cell mass 6 as described herein for increasing the electrical resistance between the poles. In a preferred embodiment, the low-conductivity membrane 2 is a cylindrical portion of the capsule having an inner diameter of 150–300μ, and extending from the point of contact with the cell mass for a total width of about 100μ–500μ.

Since the low-conductivity membrane 2 increases the resistance between the poles, the lower the conductivity of the low-conductivity membrane, the more the electrical resistance will be increased, and the better the system will perform. A bio-compatible low-conductivity material, such as a fluoroelastomer, e.g., polytetrafluoroethylene (TEFLON™), a polymethylsiloxane, nylon or other polymeric material is preferred for the low-conductivity membrane 2. It will be appreciated that the low-conductivity membrane may be permeable to certain materials, provided that it provides the requisite increase in electrical resistance. The increased resistance to short-circuiting of the present invention is achieved by reducing or preventing flow through the membrane 1 along the likely short-circuit pathways between the + and − poles of the cell mass shown in detail in FIG. 5. In a preferred embodiment, as shown in FIG. 2, the diameter of the low-conductivity membrane 2 and the circumference of the cell mass 6 between the + and − poles are substantially equal so that there remains little or no electrolytic solution 8 between the cells 6 and an inner surface of the low-conductivity membrane 2. Such intervening electrolytic solution would offer a relatively low resistance electric current flow pathway that would short-circuit the poles of the cell mass.

The tight coupling between the capsule membrane 2 and cell mass 6 limits the permissible value of the inner diameter of the capsule 1 to slightly less than the diameter of cell mass 6. The capsule inner diameter is preferably on the order of 150–300 microns. The diameter provides a good ratio of the surface-area of the capsule to the volume of material within the capsule to allow maximum diffusion of nutrients and other materials to and from the cell mass. Also, the ratio is sufficient to enable the use of membranes with lower permeability. It also makes it possible to introduce the capsules subcutaneously, when necessary by means of a small diameter hypodermic needle.

The inner surface of the membrane 2 is preferably processed or made from a material so that cells 6 tend to adhere to it. For example, the inner surface may be coated with a material which cells tend to adhere to, e.g., Con A or Polylysine L, or a high voltage electric current may be discharged through the membrane to increase the adhesion of the cell mass. While the inner portion of the low-conductivity membrane may be porous, to it is preferable to keep this layer very thin, preferably about 1 micron, since a thicker layer might enable a short circuit layer to form. Obviously, all of the materials used in the capsule are bio-compatible.

The semi-permeable membrane 4 includes pores for enabling nutrients and waste materials to diffuse to and from the cell mass 6 through a cavity 22 filled with the medium.

The semi-permeable membrane 4 should be permeable to relatively small molecules, up to molecular weights of 30,000–50,000, and impermeable to larger molecules, such as proteins and cell anti-bodies. The porosity of the semi-permeable membrane 4 is preferably the minimum necessary for the maintenance of the cell mass 6. In other words, the inward diffusion of nutrients and $O_2$, and the outward diffusion of metabolites and $CO_2$ and excretions should be sufficient to support long term cell survival, while maximizing the electrical resistance of the membrane. The semi-permeable membrane 4 must also be bio-compatible compatible and may be, for example, PSF (polysulfone) and PVC/PAN (polyvinylchloride/polyacrylonitrile) polymers such as a polyvinyl chloride acrylic copolymer. The semi-permeable membrane preferably has a thickness on the order of 50 microns, with the discriminating semi-permeable portion of the membrane having a thickness on the order of 1–2 microns. Such membranes are commercially available as hollow fibers.

As shown in FIG. 2, the center of the cell mass 6 is positioned at the inner surface of the low-conductivity ring 2. Thus, the electric resistance between the cells along opposite ends of the cell mass 6, for example cells at points A and B, is high. In the embodiment shown in FIG. 3, the cell mass 6 is positioned near the junction 20 between the semi-permeable membrane 4 and the low-conductivity membrane 2, but within the low-conductivity portion 2. A cavity 12 filled with the medium is defined between the low-conductivity membrane 2 and the cell mass. In either case, the electric potential across the cells will not be short-circuited and the recordable electric signal will be significantly improved.

Figure 6A:
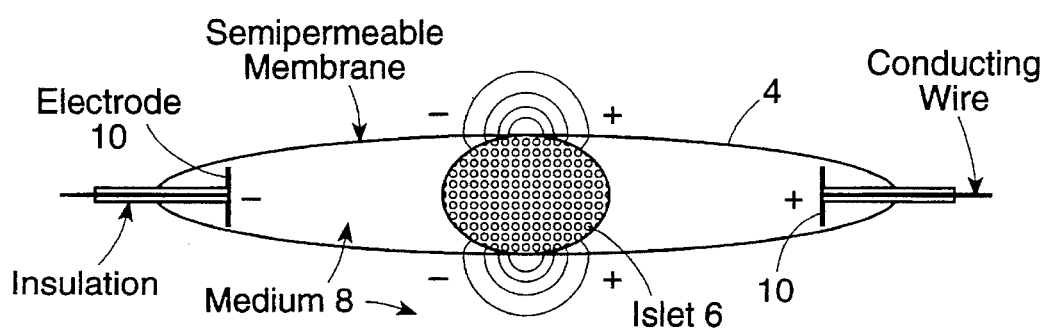
FIGS. 6A–6B show schematic views comparing the electrical fields generated by islets when not encapsulated, and when encapsulated in;the capsule of the present invention.
Figure 6B:
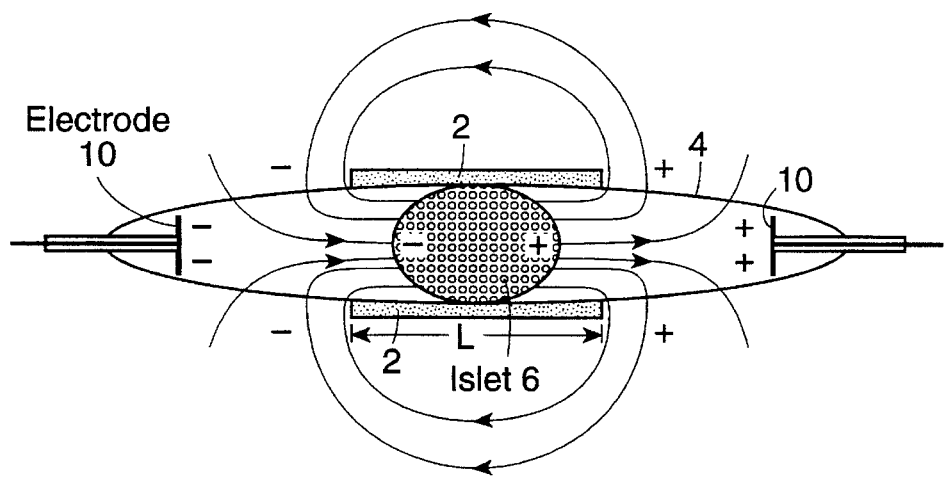

FIGS. 6A and 6B show the difference in the electric field around a cell mass 6 in a capsule without a low-conductivity membrane 2 (FIG. 6A) and a capsule with a low-conductivity membrane 2 according to the present invention (FIG. 6B). The further the low-conductivity ring 2 extends beyond the cell mass 6, the larger the electric dipole moment and the larger the measurable signal from the cell mass 6 will be. However, the length L of low-conductivity ring 2 may not be increased without limit. As the ring length is increased, the diffusion distance for nutrients, etc. through the semi-permeable membrane 10 and up to the cell mass 6 would become too large for survival or optimal functionality of the cell mass 6. A length L of 3–10 times the diameter of the cell mass is preferred.

As shown in FIG. 4, in an alternative embodiment, a low-conductivity cylinder 2, about 0.2–0.5 mm in length, may be inserted into a semi-permeable capsule 4. The low-conductivity cylinder 2 should completely seal with the outer diameter of the cell mass 6 which is disposed in the center of the low-conductivity cylinder 2.

Figure 7:
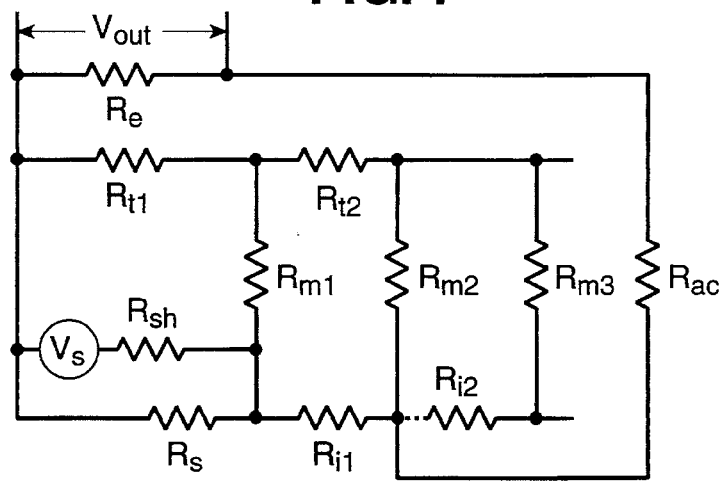
FIG. 7 shows an equivalent resistance circuit for a cell mass implanted in the capsule of the present invention.

An estimate of the improvement in the detectable output voltage from a sub- or intra-cutaneous implant using the capsule discussed herein is shown in Table 1 and FIGS. 7–10. These calculations are based upon an electric equivalent circuit which models the cell mass as a voltage generator within the capsule which is placed in a volume conductor with properties similar to those around a sub- or intra-cutaneous implant. The equivalent circuit is shown in FIG. 7, and the terms therein defined in Table 1. Table 1 also shown baseline values for each of the modelled components of FIG. 7, as measured, or best estimates.

TABLE 1

| Symbol | Resistance KOhms | Description |
| --- | --- | --- |
| $R_s$— | 100 | Source internal resistance. |
| $R_{sh}$— | 500 | Shunt - leak between cell mass & membrane. |
| $R_{i1}, R_{i2}$... | 500 | Capsule axial resistances |
| $R_{m1}, R_{m2}$... | 100 | Capsule radial resistances. |
| $R_{t1}, R_{t2}$... | 10 | Tissue resistances near capsule surface. |
| $R_{ae}$— | 10 | Tissue resistance between implanted electrodes & external electrodes. |
| $R_e$— | 100 | Tissue resistance between external electrodes. |
| $V_s$— | | Signal source in cell mass. |
| Vout— | | Externally measured signal. |

Figure 8:
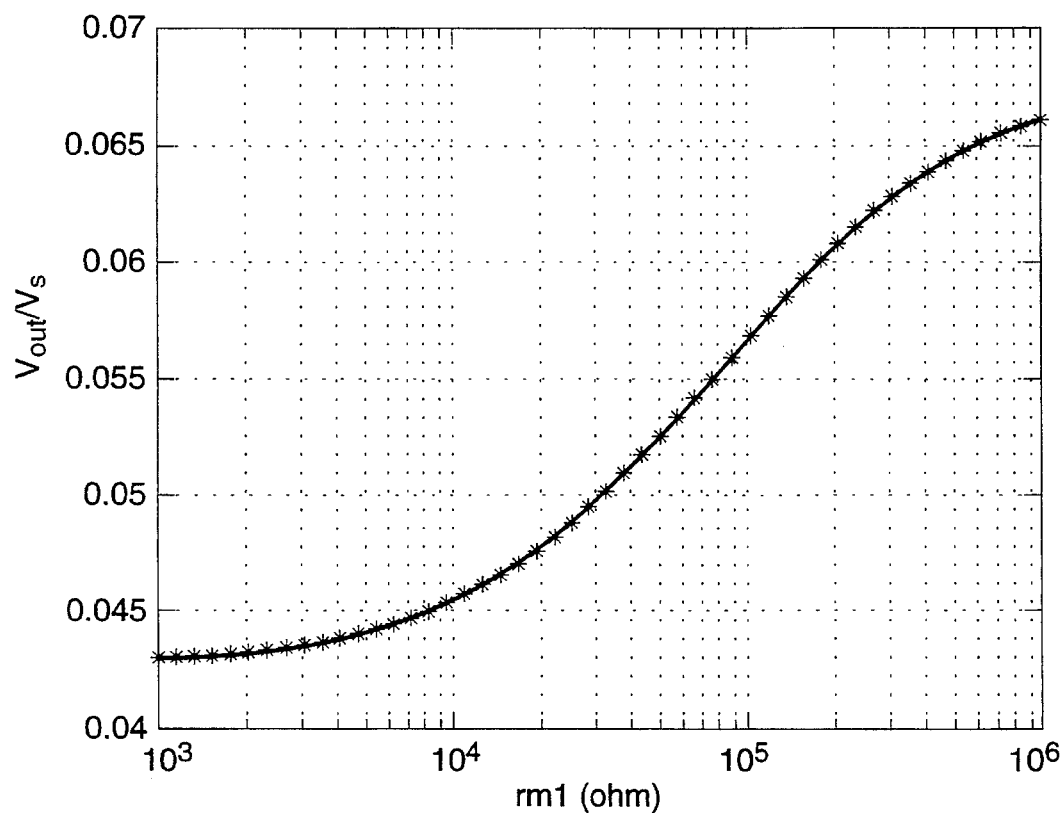
FIGS. 8–10 show graphs of the detectable voltage from a cell mass in response to changes in the resistance between poles of the cell mass.
Figure 9:
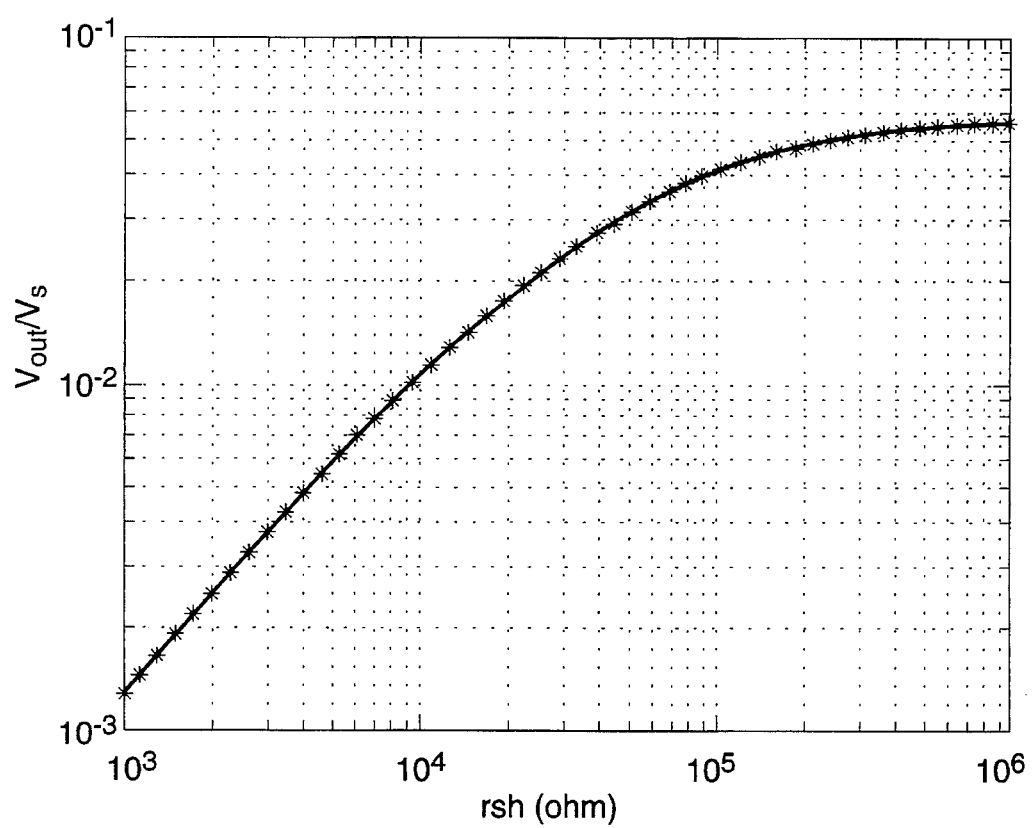
Figure 10:
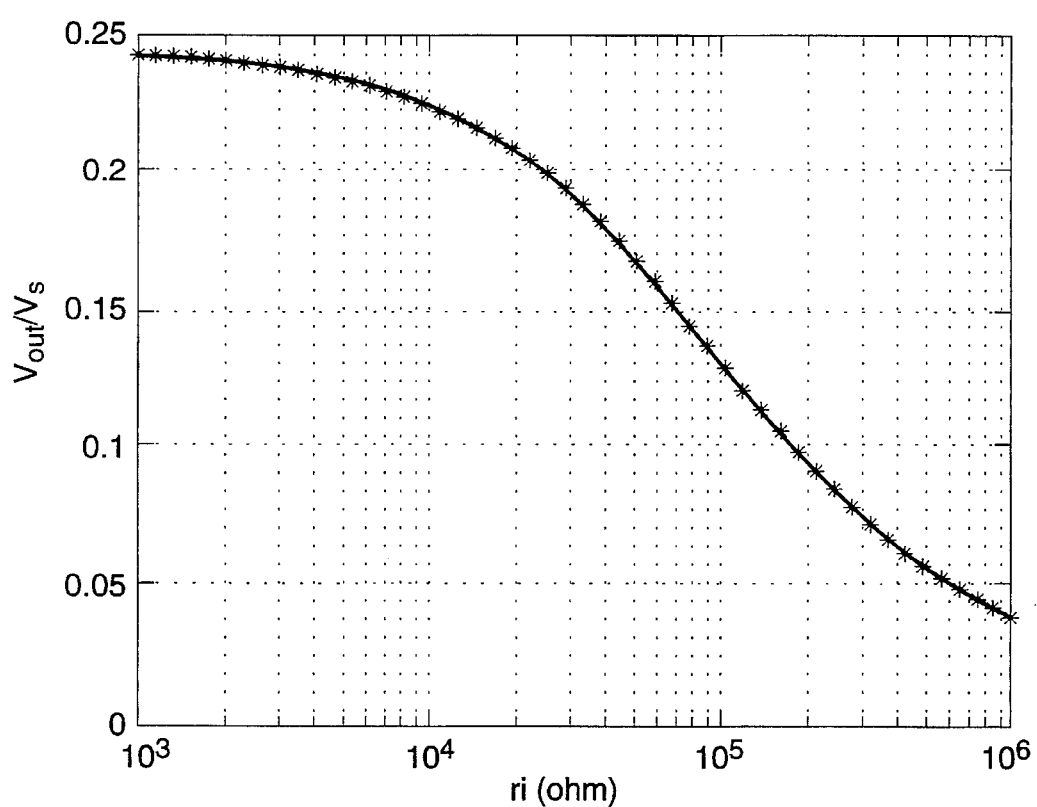

Using the equivalent circuit, the signal amplitude at the skin surface $V_{out}$ relative to the voltage generated by the cell mass $V_S$ is compared. In FIG. 8, the shunt resistance between the poles across the inner surface of the non-conductive membrane is varied while all other values are left unchanged. The signal attenuation is decreased by up to a factor of 100 when the shunt resistance is increased. FIGS. 9 and 10 show equivalent graphs for changes in the capsule axial and radial resistances as well.

The low-conductivity ring can be formed, for example, by any of the several methods:

The entire capsule can be made of the low-conductivity membrane material. The low-conductivity ring may then be masked while pores are made in the semi-permeable portion of the capsule by any conventionally known process.

The low-conductivity membrane may also be obtained by providing a much thicker membrane over the low-conductivity portion of the capsule. The much thicker membrane could be of the same material or a different material as the semi-permeable portion of the capsule.

The low-conductivity ring area could also be coated, plated or wrapped by a low-conductivity material, such as the material from which the semi-permeable membrane is constructed, after the pores are made in the semi-permeable membrane. The highest resistance to short circuiting would be obtained when the internal face of the membrane ring 2 is made low-conductivity.

Finally, the capsule can be constructed from cylinders made out of two different materials, one of which is a regular semi-permeable membrane and the other is a permeable or non-permeable membrane with very low conductivity. The parts may be assembled by adhesive, heat, etc.

While most commonly used semi permeable membranes for cell implantation are not electrically charged so that they are permeable to both non electrolytes and electrolytes, the electric resistance of the membrane can be further raised by using charged membranes which interfere with the penetration of ions and charged molecules. However, the membrane may only be mildly charged, since some permeation into the capsule by charged particles is required for essential materials such as certain amino acids, etc. Since the regular ions of the medium (sodium, potassium, etc.) are not consumed by the cells, the membrane need not be permeable to these elements.

Electric potential measurements are preferably made by electrodes 10 (FIG. 2) positioned either inside the capsule near each end, in contact with the cell mass, or in the external conducting volume. Measurements can also be performed between one internal electrode and one external electrode. In any case, the semi-permeable membrane 4 encloses the capsule at least one of the + and − poles of the cell mass 6. The end of the capsule toward the other pole may be enclosed by a semi-permeable membrane, as shown in FIG. 2, or by a low-conductivity membrane, as shown in FIG. 3. The electrodes are preferably constructed from a bio-compatible material such as platinum or gold. The wire leads connecting the electrodes with the measurement system are electrically insulated.

The electrodes are preferably connected either directly or through an amplifier to a potential detector. In the alternative, the electrodes may terminate below the skin surface at a distance from the capsule and generate a large dipole moment in the tissue. This dipole moment may be detected from electrodes on the skin surface and processed accordingly.

Although the present invention has been described in detail with respect to certain embodiments and examples, variations and modifications exist which are within the scope of the present invention as defined in the following claims.

I claim:

1. In an improved system for detecting a constituent or a condition in a patient having:

an implantable mass of living cells producing a potential difference or an electrical signal between at least a first pole on the cell mass and at least a second pole on the cell mass in response to the constituent or the condition in a medium surrounding the cells, the cell mass having at least one polar axis; and means for detecting the potential difference or electrical signal;

the improvement comprising:

a capsule surrounding the cell mass in the medium, the capsule comprising:

a low-conductivity membrane having an inner surface in sealing contact with an outer surface of the cell mass along an outer periphery of the cell mass between the first and second poles to prevent a short circuit between the poles, the low-conductivity membrane having a length extending generally in the direction of the polar axis for a sufficient extent to increase electrical resistance between the poles sufficiently to detect the electrical signal; and a semi-permeable membrane comprising pores for enabling nutrients and waste materials to diffuse to and from the cell mass, the semi-permeable membrane enclosing at least the first pole of the cell mass and forming a first cavity filled with the medium between the semi-permeable membrane and the enclosed pole.

2. The system according to claim 1 wherein the low-conductivity membrane is a cylindrical ring.

3. The system according to claim 2 wherein:

the low-conductivity membrane encloses at least the second pole and forms a second cavity between the low-conductivity membrane and the second pole, the second cavity filled with the medium; and the means for detecting the potential difference or electrical signal comprises an electrode in the second cavity connected to an electrically conductive lead extending through the low-conductivity membrane, and a second electrode in contact with or in close proximity to the first pole.

4. The system according to claim 1 wherein:

the low-conductivity membrane encloses at least the second pole and forms a second cavity between the low-conductivity membrane and the second pole, the second cavity filled with the medium; and the means for detecting the potential difference or electrical signal comprises an electrode in the second cavity connected to an electrically conductive lead extending through the low-conductivity membrane, and a second electrode in contact with or in close proximity to the first pole.

5. The system according to claim 1 wherein the semi-permeable membrane encloses the first and second poles.

6. The system according to claim 1 wherein the semi-permeable membrane is electrically charged.

7. The system according to claim 1 wherein the means for detecting the potential difference or electrical signal comprises an electrode in contact with or in close proximity to each pole.

8. The system according to claim 1 wherein the capsule is formed by the steps of:

a) forming the capsule of a low-conductivity material;

b) masking a portion of the capsule constituting the low-conductivity membrane; and c) forming pores in an unmasked portion of the capsule to form the semi-permeable membrane.

9. The system according to claim 1 wherein the low-conductivity membrane comprises a thick layer of a permeable material.

10. The system according to claim 1 wherein the capsule is formed by the steps of:

a) forming the capsule of a semi-permeable material; and b) coating a portion of the capsule constituting the low-conductivity membrane with a low-conductivity material.

11. The system according to claim 1 wherein the capsule is formed by the steps of:

a) providing a low-conductivity cylinder for forming the low-conductivity membrane;

b) providing a semi-permeable material for forming the semi-permeable membrane; and c) attaching the low-conductivity cylinder to the semi-permeable material.

12. A capsule for surrounding an implantable cell mass in a medium for improving an electrical signal detectable from the living cell mass, the living cells producing the electrical signal between at least a first pole on the cell mass and at least a second pole on the cell mass in response to a condition or constituent in a medium surrounding the cells, the cell mass having at least one polar axis, the capsule comprising:

a low-conductivity membrane having an inner surface adapted to be in sealing contact with an outer surface of the cell mass along an outer periphery of the cell mass between the poles to prevent a short circuit between the poles, the low-conductivity membrane having a length extending generally in the direction of the polar axis for a sufficient extent to increase electrical resistance between the poles sufficiently to detect the electrical signal; and a semi-permeable membrane comprising pores for enabling nutrients and waste materials to flow to and from the cell mass, the semi-permeable membrane enclosing at least one of the poles of the cell mass and forming a first cavity filled with the medium between the semi-permeable membrane and the pole.

13. In an improved system for detecting a constituent or a condition in a patient having:

an implantable mass of living cells producing a potential difference or an electrical signal between at least a first pole on the cell mass and at least a second pole on the cell mass in response to the constituent or the condition in a medium surrounding the cells, the cell mass having at least one polar axis; and means for detecting the potential difference or electrical signal;

the improvement comprising:

a low-conductivity membrane having an inner surface in sealing contact with an outer surface of the cell mass along an outer periphery of the cell mass between the first and second poles to prevent a short circuit between the poles, the low-conductivity membrane having a length extending generally in the direction of the polar axis for a sufficient extent to increase electrical resistance between the poles sufficiently to detect the electrical signal.

* * * * *